United States Patent [19]

Takago

[11] 4,248,993
[45] Feb. 3, 1981

[54] ROOM TEMPERATURE CURABLE ORGANOPOLYSILOXANE

[75] Inventor: Toshio Takago, Annaka, Japan

[73] Assignee: Shin-Etsu Chemical Co. Ltd., Tokyo, Japan

[21] Appl. No.: 63,172

[22] Filed: Aug. 3, 1979

Related U.S. Application Data

[63] Continuation of Ser. No. 917,660, Jun. 21, 1978, Pat. No. 4,180,642.

[30] Foreign Application Priority Data

Jun. 29, 1977 [JP] Japan .................................. 52-77590

[51] Int. Cl.³ ............................................ C08G 77/26
[52] U.S. Cl. ........................................ 528/38; 528/28; 556/415; 556/424; 528/32; 528/34; 528/42; 528/43; 528/901; 260/37 SB; 260/45.75 R; 260/45.75 B
[58] Field of Search ................. 260/448.2 N, 448.2 E; 528/28, 38; 556/415, 424

[56] References Cited

U.S. PATENT DOCUMENTS

| | | | |
|---|---|---|---|
| 3,819,563 | 6/1974 | Takago et al. | 528/901 |
| 4,020,044 | 4/1977 | Crossan et al. | 528/901 |
| 4,180,642 | 12/1979 | Takago | 528/32 |

Primary Examiner—Melvyn I. Marquis
Attorney, Agent, or Firm—Toren, McGeady and Stanger

[57] ABSTRACT

Novel room temperature curable organopolysiloxane compositions which are stable as ready mixed for a long period of time when kept in an air-tight container and readily curable at room temperature to form rubber-like elastomers when exposed to the moisture-containing air. The composition comprises a diorganopolysiloxane terminated at both chain ends with hydroxy groups, an organosilane having in a molecule 3 or 4 substituted or unsubstituted vinyloxy groups or a partial hydrolysis-condensation product thereof, and an organosilane or an organopolysiloxane having in a molecule at least one monovalent group expressed by the general formula of the type $(R_2N)_2C=N-$, where R is a hydrogen atom or a monovalent hydrocarbon group. The compositions are free from toxicity and offensive odor as well as corrosiveness against various substrate surfaces, especially of metals.

5 Claims, No Drawings

ROOM TEMPERATURE CURABLE ORGANOPOLYSILOXANE

This is a continuation of application Ser. No. 917,660, filed on June 21, 1978 now U.S. Pat. No. 4,180,642.

BACKGROUND OF THE INVENTION

The present invention relates to a novel room temperature curable organopolysiloxane composition storable as one package with extended storability in a tightly sealed vessel and with improved curability in the open air atmosphere.

In the prior art, various types of room temperature curable organopolysiloxane compositions are known which are stable in a tightly sealed vessel and curable in the open air atmosphere even at room temperature by reaction with atmospheric moisture to be converted into a rubber-like elastomer. These organopolysiloxane compositions fall into two classes, i.e., (1) two-package type where the contents of two separate packages are mixed just prior to use and (2) one-package type where the compositions are mixed and stored in one package. The compositions of the latter type are prevailing in general owing to convenience in use as a sealing material, caulking material, adhesive material and the like.

The one-package type room temperature organopolysiloxane compositions are also classified into several groups according to the mechanisms of their crosslink formation by condensation reaction evolving carboxylic acids, amines, oximes or alcohols as the condensation products. Among the four groups of the compositions, the first three have the disadvantages that the carboxylic acids, amines or oximes liberated by the condensation reaction in the crosslink formation in air are toxic or corrosive with offensive odors so that powerful ventilation is indispensable in the use of the compositions as well as the necessity of primer treatment prior to use in order to prevent rusting of a metal substrate.

On the other hand, the compositions curable by the mechanism of dealcoholation condensation are free from the problems due to the formation of toxic or corrosive gases. However, they suffer from the problems of their poor storability as well as rather slow curing velocity at room temperature, especially in the depths farther from the surface, and the poor mechanical properties or brittleness of the cured products. In addition, the alkoxy titanate compounds as the curing accelerator necessitated in these compositions remain in the cured products and cause coloration or lowering of thermal stability to the product.

Similarly, the metal salts of organic acids used at the curing catalyst in the compositions curable by the mechanisms of liberating carboxylic acids, oximes or alcohols also remain in the cured products, sometimes resulting in offering some problems due to their toxicity.

Recently, room temperature curable organopolysiloxane compositions of a novel type have been disclosed in U.S. Pat. No. 3,819,563 according to which the compositions are cured by the atmospheric moisture liberating a ketone. These compositions are free from the problems with respect to adhesiveness or corrosiveness, but still not satisfactory due to unpleasant odors emitted in the course of curing.

SUMMARY OF THE INVENTION

The object of the present invention is therefore to provide a novel room temperature curable organopolysiloxane composition of one-package type having an excellent curability at room temperature which are free from the above-described problems encountered in the prior art compositions with respect to the evolution of toxic gases in the course of curing and coloration or discoloration after a prolonged storage, and also free from the inclusion of metal salts of organic acids.

The composition of the present invention comprises
(a) 100 parts by weight of a diorganopolysiloxane terminated at both chain ends with hydroxy groups, represented by the general formula $HO\text{-}(R_2Si\text{-}O)_{\overline{n}}H$ where R is a monovalent hydrocarbon group and n is a positive integer,
(b) from 1 to 25 parts by weight of a vinyloxy-containing silane represented by the general formula

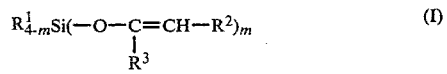

$$R^1_{4-m}Si(-O-C=CH-R^2)_m \quad (I)$$
$$\phantom{R^1_{4-m}Si(-O-}R^3$$

where $R^1$ is a substituted or unsubstituted monovalent hydrocarbon group, $R^2$ and $R^3$ are each a hydrogen atom or a substituted or unsubstituted monovalent hydrocarbon group and m is 3 or 4, or a partial hydrolysis-condensation product thereof, and
(c) from 0.01 to 10 parts by weight of an organosilane or an organopolysiloxane having, in a molecule, at least one monovalent group represented by the general formula

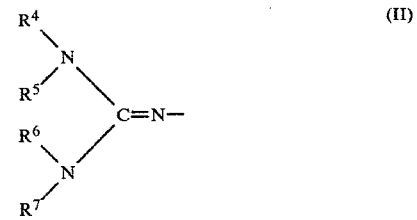

(II)

where $R^4$, $R^5$, $R^6$ and $R^7$ are each a hydrogen atom or a monovalent hydrocarbon group.

DETAILED DESCRIPTION OF THE PREFERRED EMBODIMENTS

The present invention has been completed as a result of extensive investigation by the inventor, based on the discovery that compositions comprising hydroxy-terminated diorganopolysiloxane as the base component, a silane compound having 3 or 4 of substituted or unsubstituted vinyloxy groups in a molecule as represented by formula (I) above or a partial hydrolysis-condensation product thereof and a silane or siloxane compound having at least one monovalent group represented by formula (II) above in a molecule have a very excellent stability when stored in an air-tight vessel with substantial exclusion of moisture. The same compositions are curable with sufficient velocity when exposed to the air without evolution of any toxic gas or offensive odor, to produce a cured product having a superior heat stability, and an excellent adhesion to various substrates including metals without the possibility of corrosion.

The component (a) as the base ingredient of the composition according to the present invention is a diorganopolysiloxane terminated at both chain ends with hydroxy groups and expressed by the general formula $$HO-(R_2Si-O)_nH$$

where R is a substituted or unsubstituted monovalent hydrocarbon group and n is a positive integer. Examples of the monovalent hydrocarbon groups represented by R are alkyl groups, such as methyl, ethyl, propyl, isopropyl, butyl, 2-ethylhexyl and octyl groups; cycloalkyl groups, such as cyclohexyl and cyclopentyl groups; alkenyl groups, such as vinyl, allyl and hexenyl groups; aryl groups, such as phenyl, tolyl, xylyl, naphthyl, biphenylyl and phenanthryl groups; and aralkyl groups, such as benzyl and phenylethyl groups. Included also in the examples are the substituted hydrocarbon groups, e.g. halogen-substituted hydrocarbon groups, such as chloromethyl, trichloropropyl, trifluoropropyl, bromophenyl and chlorocyclohexyl groups; and cyano-substituted hydrocarbon groups, such as 2-cyanoethyl, 3-cyanopropyl, 4-cyanobutyl and 2-cyanobutyl groups. It is preferred that the diorganopolysiloxane as the component (a) has a viscosity of at least about 25 centistokes, or preferably 1,000 centistokes at 25° C. so that the cured product may have a good rubber-like elasticity and excellent mechanical strengths.

It is optional that the hydroxy-terminated diorganopolysiloxane is mixed with a diorganopolysiloxane having terminal groups other than the hydroxy groups, e.g. trimethylsilyl groups, when the cured rubber composition is desired to have a lower hardness and larger elongation. In this case, the amount of the former diorganopolysiloxane should exceed that of the latter diorganopolysiloxane.

The component (b) used in the composition according to the present invention is a vinyloxy or ethenyloxy-containing silane or a substituted vinyloxy-containing silane expressed by formula (I) or a partial hydrolysis-condensation product thereof. This component behaves as curing agent. In formula (I), the group represented by $R^1$ is a substituted or unsubstituted monovalent hydrocarbon group, such as methyl, ethyl, propyl, vinyl and phenyl groups; $R^2$ and $R^3$ are each a hydrogen atom or a monovalent hydrocarbon group, such as methyl, phenyl, vinyl and isobutenyl groups; and m is 3 or 4. Examples of the silane compound as the component (b) are methyltrivinyloxysilane, methyltri(isopropenyloxy)silane, vinyltri(vinyloxy)silane, phenyltri(vinyloxy)silane, propyltri(isopropenyloxy)silane, tetra(isopropenyloxy)silane, methyltri(1-methyl-1-propenyloxy)silane, methyltri-(1,4-dimethyl-1,3-pentadienyloxy)silane, 3-aminopropyltri(isopropenyloxy)silane, and the like and a partial hydrolysis-condensation product thereof.

Among the above-named silane or siloxane compounds, the isopropenyloxy-containing ones are preferred to the vinyloxy-containing ones if the offensive odors of the resulting condensation products are taken into consideration.

Component (b) is used in an amount from 1 to 25 parts by weight or, preferably, from 4 to 10 parts by weight per 100 parts by weight of the component (a). This is because smaller amounts may cause premature gelation to the composition in the course of its preparation or during storage, resulting in forming cured products having unsatisfactory properties, while larger amounts may bring about excessive shrinkage to the composition by curing as well as inferior elasticity to the resultant cured products.

The vinyloxy-containing silane compounds as the component (b) can be synthesized by the dehydrochlorination reaction of a halogenosilane and a corresponding ketone or aldehyde in the presence of an acid acceptor, such as an organic amine, e.g. triethylamine, N,N-dimethylaniline and the like, or metallic sodium and, if necessary, a catalyst, such as zinc chloride and the like.

The component (c) used in the compositions is an organosilane or organopolysiloxane having, in a molecule, at least one of the groups represented by formula (II) above. The component plays a role as an auxiliary curing agent cooperative with the component (b). In formula (II), the groups represented by $R^4$, $R^5$, $R^6$ and $R^7$ are each a hydrogen atom or a monovalent hydrocarbon group, preferably methyl, ethyl, propyl or phenyl group. The group represented by formula (II) may be bonded to the silicon atom with a divalent group of any kind intervening, the divalent group being usually an alkylene or oxyalkylene group.

Preferably, the component (c) is a silane compound represented by the general formula

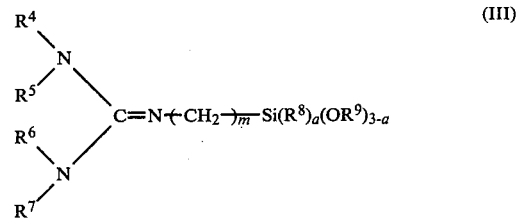
(III)

where m is a positive integer of 2, 3 or 4, a is 0, 1 or 2, $R^4$, $R^5$, $R^6$ and $R^7$ are each the same as defined above, $R^8$ is a monovalent hydrocarbon group having 1 to 6 carbon atoms, and $R^9$ is an alkyl group having 1 to 4 carbon atoms, or a partial hydrolysis-condensation product thereof.

Especially recommendable as the component (c) are the silane compounds expressed by formula (III) where each of $R^4$ to $R^9$ is a methyl group, m is 3 and a is 0, 1 or 2, such silane compounds being expressed by the formula

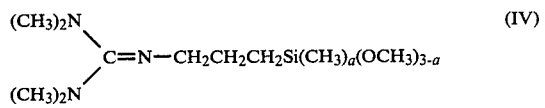
(IV)

Examples of the component (c) are the compounds expressed by the following structural formulas, in which symbols Me, Et, Pr and Ph denote methyl, ethyl, propyl and phenyl groups, respectively.

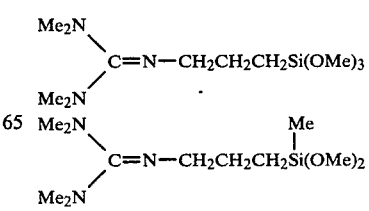

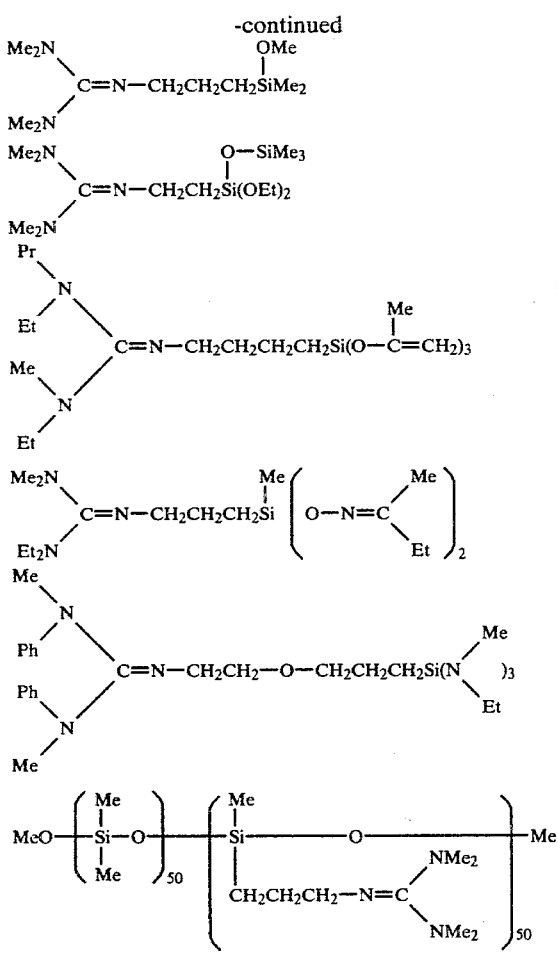

Among the above-named silane and polysiloxane compounds, the most preferred is the silane compound expressed by the first formula owing to its easy formulation.

The amounts of the component (c) in the composition of the present invention may range from 0.01 to 10 parts by weight or, preferably, from 0.1 to 1 part by weight per 100 parts by weight of the component (a). Any smaller amounts disadvantageously result in prolonged tack-free time when the stock is exposed to the atmosphere and insufficient curing in the depths of the stock. On the other hand, any larger amounts result in shortening tack-free time to only a few seconds, bringing about working inconvenience.

The compounds suitable for use as the component (c) can be readily synthesized, for example, by reacting guanidine or its derivatives with a silane or a polysiloxane having one or more halogen-substituted alkyl groups in the presence of an appropriate acid acceptor.

The composition of the present invention may, in addition to the above-described components (a), (b) and (c), contain a variety of fillers. Illustrative of the fillers are siliceous fillers, such as finely divided fused quartz powder, silica aerogel, socalled fumed silica blocked on the surface with organosiloxy groups, precipitated silica, and diatmaceous earth; metal oxides, such as iron oxides, zinc oxide, aluminum oxide, and titanium dioxide; metal carbonates, such as calcium carbonate, magnesium carbonate, and zinc carbonate; asbestos; glass wool; carbon black; mica powder; pulverized synthetic resins, such as polystyrene, polyvinyl chloride, and polypropylene. The amount of the filler to be included in the composition is not limitative insofar as no remarkable disadvantages are brought about to the properties of the resulting composition. It is recommended that the filler is thoroughly dried prior to use.

The compositions of the present invention may also contain various known additives, such as pigments, dyes, aging retarders, anti-oxidants, anti-static agents, flame retardants, e.g. antimony oxide and chlorinated paraffin, thermal conductivity improvers, e.g. boron nitride, heat stability improvers, e.g. ceric oxide, and sagging reducing agents, e.g. polypropylene glycol, as well as metal salts of carboxylic acids, metal alcoholates, and the socalled carbon-functional silanes having an amino group, epoxy group, mercapto group or the like, which serve as adhesion improvers.

The compositions of the present invention are prepared readily by uniformly blending the above-described components (a), (b) and (c) together with the fillers and other optional additives in a dry atmosphere.

The compositions of the present invention can be stable over a long period of time when stored in an airtight vessel, and readily cured when exposed to the atmospheric air by reaction with the atmospheric moisture. The cured composition can firmly adhere to the surfaces of various substrates, especially metals. No toxic or corrosive gases are formed when the compositions cure. No rust is produced on the metal surfaces so that the compositions are useful as a sealing material, caulking material, adhesive material, coating material, water repellent, fiber treatment agent, mold releasing agent and the like. If necessary, the composition may be used as diluted with an organic solvent, such as hydrocarbon solvents, e.g. toluene and petroleum ether, ketones, and esters.

The present invention will further be illustrated by way of several examples following. The component (b) methyltri(isopropenyloxy)silane and the component (c) expressed by the formula

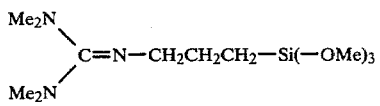

both to be employed in the examples were prepared by Formulations I and II, respectively, as follows.

Formulation I

Into a 2-liter glass autoclave were introduced 100 g of benzene, 250 g (2.47 moles) of triethylamine, 232 g (4.0 moles) of acetone, 1.0 g of anhydrous zinc chloride and 120 g (0.8 mole) of methyltrichlorosilane, and the resultant mixture was heated gradually to 110° C., followed by continuous agitation for 16 hours. The pressure inside the autoclave was 2.3 kg/cm²G at the beginning and 1.0 kg/cm²G at the end of the reaction. As the temperature of the mixture reached around 110° C., a white crystalline material began precipitating, the precipitate being identified to be the hydrochloride of triethylamine. The reaction mixture was then cooled to room temperature, and taken out of the autoclave and filtered to separate the precipitated triethylamine hydrochloride in a quantitative amount weighing about 320 g. The filtrate was subjected to distillation under reduced pressure at 4 mmHg and then rectification at 20 mmHg, to produce 83 g of a fraction boiling at 73° C. under 20 mmHg.

The above obtained fraction was mixed with 8 g of active carbon and the mixture was heated at 50° to 60° C. for 4 hours to remove any trace amounts of hydrogen chloride and subjected to a second distillation, to give a product having a refractive index of 1.4246 at 25° C. The product was identified to be methyltri(isopropenyloxy)silane by means of gas chromatography, infrared absorption spectrum and elementary analysis for silicon.

Formulation II

Into a 1-liter four-necked flask equipped with a thermometer, a condenser, an inlet tube for nitrogen gas and an outlet tube for vent gases were introduced 345 g (3 moles) of 1,1,3,3-tetramethylguanidine and 208 g (1 mole) of 3-chloropropyltrimethoxysilane. The mixture was heated to 120° to 130° C., followed by continuous agitation for 4 hours and then cooling to room temperature. The reaction mixture was filtered to separate as the precipitate 145 g of the hydrochloride of 1,1,3,3-tetramethylguanidine. The filtrate was subjected to distillation at 150° C. under reduced pressure at 10 mmHg, and then rectification under high vacuum to produce 120 g of a fraction boiling at 118° C. under 5 mmHg, the yield corresponding to 42% of the theoretical.

The compound thus obtained was a colorless, transparent liquid having a density $d_4^{20}$ of 1.07 and a refractive index $n_D^{25}$ of 1.4761, and identified to have the structural formula

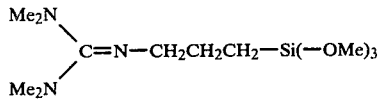

by means of infrared absorption spectral analysis, according to which the presence of the groups of —Si—O—Me, —N—Me and —C=N— was indicated by the absorption bands of 1045, 1200 and 1620 cm$^{-1}$, respectively, with the absence of an absorption band to be assigned to the group =N—H.

In the following examples, parts are all parts by weight. The mechanical properties, i.e. hardness, tensile strength and ultimate elongation, as expressed in the examples were determined for a rubbery elastomer sheet 2 mm thick that had been prepared from each composition and kept in an atmosphere of a 55% relative humidity at 23° C. for 7 days in accordance with the procedure specified in JIS C 2123, items 8 and 9. The heat stability of each cured composition was evaluated by determining the above mechanical properties of the elastomer sheets as just cured or after 5 days at 150° C. or 200° C. The adhesivity of each composition was determined by measuring the force used in separating from each other two aluminum plates 25 mm wide that had been bonded with the composition cured, over an overlapping length of 10 mm.

Besides the above testing, the corrosiveness of each composition was examined for a copper plate coated with the composition and kept at 50° C. for 7 days in a humid atmosphere in accordance with the procedure specified in MIL A 46146 by visual inspection of the copper surface for the presence or absence of green dust. In any of the examples, no corrosion was found occurring.

EXAMPLE 1

A blend of 100 parts of a dimethylpolysiloxane terminated at both chain ends with hydroxy groups and having a viscosity of 20,500 centistokes at 25° C. and 12 parts of a fumed silica filler with its surface treated with trimethylchlorosilane and having a specific surface area of 200 m$^2$/g was passed once through a three-roll mill. To the resulting mixture were added 6 parts of methyltri(isopropenyloxy)silane prepared by Formulation I and 0.5 part of the silane compound prepared by Formulation II in a dry atmosphere, followed by defoaming treatment, to produce the desired composition.

The adhesivity of the composition and the mechanical properties reflected by the heat stability of the cured rubbery elastomer are set out in Table I that will be given hereinafter. In the course of curing of the composition, no unpleasant odor came out.

The composition prepared as above was found stable over a period of at least 6 months' storage in an air-tight vessel. That is to say, no coloration or discoloration of the composition took place during the storage, and when the thus stored composition was kept in an atmosphere of a 55% relative humidity at 23° C. for 7 days to cure, a rubbery elastomer having nearly the same properties as above could be produced.

EXAMPLE 2

A blend of 100 parts of the same dimethylpolysiloxane as used in Example 1 and 12 parts of a fumed silica filler with its surface treated with trimethylchlorosilane and having a specific surface area of 130 m$^2$/g was passed once through a three-roll mill. To the resulting mixture were added 6 parts of vinyltri(isopropenyloxy)silane prepared in a manner similar to Formulation I, 6 parts of 3-aminopropyltri(isopropenloxy)silane, 1 part of 3-aminopropyltriethoxysilane and 0.5 part of the silane compound prepared by Formulation II in a dry atmosphere, followed by defoaming treatment, to produce the desired composition.

The adhesivity of the composition and the mechanical properties reflected by the heat stability of the cured rubbery elastomer are set out in Table I. During the curing of the composition, tack-free time was about 10 minutes and the curing velocity was estimated at 2 to 3 mm per day from the surface to the depth. The cured elastomer exhibited a good adhesivity to the surfaces of various materials, such as glass, copper, epoxy resin, phenolic resin, and polyester resin, as well as aluminum.

The composition could be stored in an air-tight vessel at 20° C. for at least 6 months without coloration or discoloration, and the thus stored composition, uncured or cured, exhibited the same curability, properties, corrosiveness, or adhesiveness as possessed by the fresh composition or the elastomers thereof just cured.

EXAMPLE 3

A blend of 90 parts of a dimethylpolysiloxane terminated at both chain ends with hydroxy groups and having a viscosity of 7,580 centistokes at 25° C., 10 parts of a dimethylpolysiloxane terminated at both chain ends with trimethylsilyl groups and having a viscosity of 100 centistokes at 25° C. and 15 parts of a fumed silica filler with its surface treated with a dimethylpolysiloxane and having a specific surface area of 180 m$^2$/g was passed once through a three-roll mill. To the resulting mixture were added 8 parts of tetra(isopropenyloxy)silane prepared in a manner similar to Formulation I, 0.5 part of 3-aminopropyltriethoxysilane and 0.7 part of a silane compound expressed by the following structural formula

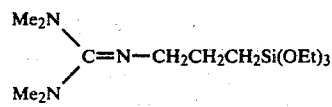

prepared in a manner similar to Formulation II in a dry atmosphere, followed by defoaming treatment, to produce the desired composition.

The adhesivity of the composition and the mechanical properties reflected by the heat stability of the cured rubbery elastomer are set out in Table I. During the curing, the tack-free time was about 4 minutes and the curing velocity was estimated at 2 to 3 mm per day from the surface to the depth.

The composition could be stored in an air-tight vessel at 20° C. for at least 6 months without coloration or discoloration, and the thus stored composition, uncured or cured, exhibited the same curability, properties, corrosiveness, or adhesiveness as possessed by the fresh composition or the elastomers thereof just cured.

EXAMPLE 4

To 100 parts of a methylvinylpolysiloxane terminated at both chain ends with hydroxy groups and hving a viscosity of 65,800 centistokes at 25° C., of which the content of the vinyl groups was 5 mole % of all organic groups, was added 13 parts of a fumed silica filler having a specific surface area of 200 m²/g and mixed on a kneader at 150° C. for 2 hours. To the resulting mixture were added 8 parts of vinyltri(1-isobutenyloxy)silane prepared in a manner similar to Formulation I, 0.5 part of a silane compound expressed by the following structural formula

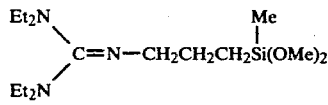

and 0.5 part of a silane compound expressed by the structural formula

NH$_2$CH$_2$CH$_2$NH—CH$_2$CH$_2$CH$_2$Si(OMe)$_3$ in a dry atmosphere, followed by defoaming treatment, to produce the desired composition.

The adhesivity of the composition and the mechanical properties reflected by the heat stability of the cured rubbery elastomer sheets are set out in Table I. During the curing, the tack-free time was about 8 minutes.

Slight discoloration took place to the composition when stored in an air-tight vessel at 20° C. for 6 months.

EXAMPLE 5

A blend of 100 parts of a dimethylpolysiloxane terminated at both chain ends with hydroxy groups and having a viscosity of 28,400 centistokes at 25° C. and 30 parts of a calcium carbonate filler (Whiton SSB, product of Shiraishi Calcium Co., Japan) was mixed with 6.0 parts of phenyltri(isopropenyloxy)silane prepared in a manner similar to Formulation I, 1 part of a siloxane compound expressed by the following structural formula

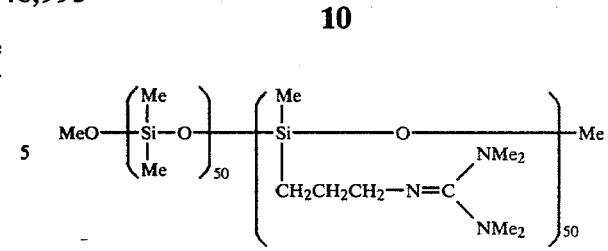

and 0.5 part of 3-aminopropyltriethoxysilane in a dry atmosphere, followed by defoaming treatment, to produced the desired composition. During the mixing operation, the temperature of the composition was witnessed to have slightly risen to 20° to 28° C.

The composition thus produced rapidly cured upon exposure to the moisture-containing air, with the tack-free time being 4 minutes and, after 24 hours of standing in the atmosphere, became completely cured to the depth of 3 mm.

The adhesivity of the composition and the mechanical properties reflected by the heat stability of the cured rubbery elastomer are set out in Table I.

This composition was found stable when stored for 14 days in an air-tight vessel at 20° C., exhibiting no recognizable changes.

EXAMPLE 6

A blend of 100 parts of a methylphenylpolysiloxane composed of 90 mole % of dimethylsiloxane units and 10 mole % of diphenylsiloxane units terminated at both chain ends with hydroxy groups and having a viscosity of 19,600 centistokes at 25° C., 15 parts of a fumed silica filler having a specific surface area of 230 m²/g and 0.2 part of polypropylene glycol was passed once through a three-roll mill. To the resulting mixture were added 6 parts of vinyltri(isopropenyloxy)silane prepared in a manner similar to Formulation I, 1 part of 3-aminopropyltriethoxysilane and 0.5 part of the silane compound prepared by Formulation II in a dry atmosphere, followed by defoaming treatment, to produce the desired composition.

This composition was highly transparent and could be cured into a rubber-like elastomer by exposing to an atmosphere of 55% relative humidity at 23° C. for 7 days.

The adhesivity of the composition and the mechanical properties reflected by the heat stability of the cured rubbery elastomer are set out in Table I. The adhesivity of the composition was good not only to aluminum but also to various other surfaces.

The composition was stable when stored in an air-tight vessel for at least 6 months without coloration or discoloration, and the thus stored composition exhibited the same properties as those of the fresh composition.

EXAMPLE 7

A blend of 100 parts of the same dimethylpolysiloxane as used in Example 1 and 15 parts of a fumed silica filler with its surface treated with trimethylchlorosilane and having a specific surface area of 200 m²/g was passed once through a three-roll mill. To the resulting mixture were added 6 parts of vinyltri(isopropenyloxy)-silane prepared in a manner similar to Formulation I, 1 part of 3-aminopropyltriethoxysilane, 0.3 part of the silane compound prepared by Formulation II and 2.5 parts of ceric oxide in a dry atmosphere, followed by defoaming treatment, to produce the desired composition.

The adhesivity of the composition and the mechanical properties reflected by the heat stability of the cured rubbery elastomer are set out in Table I.

EXAMPLE 8

A room temperature curable composition was prepared by homogeneously mixing 70 parts of a dimethylpolysiloxane terminated at both chain ends with hydroxy groups and having a viscosity of 19,400 centistokes at 25° C., 30 parts of a dimethylpolysiloxane terminated at both chain ends with trimethylsilyl groups and having a viscosity of 5,420 centistokes at 25° C., 15 parts of a fumed silica surface-blocked with trimethylsilyl groups and having a specific surface area of 300 m²/g, 6.0 parts of vinyltri(isopropenyloxy)silane, 1.0 part of 3-aminopropyltriethoxysilane and 0.5 part of the silane compound expressed by the formula

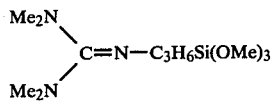

in a dry atmosphere, followed by defoaming treatment. The composition thus prepared was stable over 6 months' storage in an air-tight vessel. The adhesivity of the composition and the mechanical properties of the cured rubbery elastomer are set out in Table I.

EXAMPLE 9

A room temperature curable composition was prepared by homogeneously mixing 80 parts of a dimethylpolysiloxane terminated at both chain ends with hydroxy groups and having a viscosity of 15,400 centistokes at 25° C., 20 parts of a methylphenylpolysiloxane composed of 10 mole % of methylphenylsiloxane units and 90 mole % of dimethylsiloxane units, terminated at both chain ends with dimethylsilyl groups and having a viscosity of 546 centistokes at 25° C., 16 parts of a fumed silica filler surface-blocked with dimethylsiloxy groups and having a specific surface area of 150 m²/g, 8 parts of propyltri(isopropenyloxy)silane, 0.5 part of N-(2-aminoethyl)aminopropyltrimethoxysilane and 0.5 part of a siloxane compound expressed by the formula

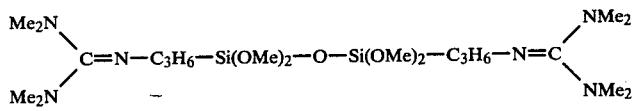

in a dry atmosphere, followed by defoaming treatment.

The adhesivity of the composition and the mechanical properties of the cured rubbery elastomer are set out in Table I.

Control 1

For purposes of comparison, the procedure of Example 6 was repeated, omitting 6 parts of vinyltri(isopropenyloxy)silane and 0.5 part of the silane compound prepared by Formulation II and, instead, using 0.1 part of dibutyl tin dilaurate and 0.5 part of diacetynyldiisopropyl titanate, the other ingredients being the same. The thus prepared composition was cured to form a sheet of rubber-like elastomer, which was then tested for hardness, tensile strength and ultimate elongation. The test results are set out in Table I.

EXAMPLES 10–15 and Control 2.

These examples and control were undertaken in order to demonstrate the criticality of the component (b) in relation to amounts included in the desired compositions.

A variety of amounts of vinyltri(isopropenyloxy)silane, i.e., 0.5 part in Control 2, 2.0 parts in Example 10, 3.5 parts in Example 11, 5.0 parts in Example 12, 8.0 parts in Example 13, 15.0 parts in Example 14 and 25.0 parts in Example 15, each were mixed with 100 parts of a dimethylpolysiloxane terminated at both chain ends with hydroxy groups and having a viscosity of 30,500 centistokes at 25° C., 15 parts of a fumed silica filler surface-blocked with trimethylsilyl groups and having a specific surfac area of 300 m²/g, 1.0 part of N-(2-aminoethyl)aminopropyltrimethoxysilane and 0.5 part of the silane compound expressed by the following formula, to obtain respective compositions.

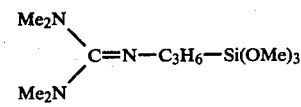

The composition obtained from Control 2 became gelled before the mixing of the various ingredients were completed and hence, the further tests were unavailable. The composition from Example 10 became gelled after storage at 70° C. for 24 hours. The composition from Example 11 exhibited a slight increase in its viscosity, while those from Examples 12–15 were found satisfactory.

The test results for the compositions and cured rubbery elastomers formed thereof from Examples 11–15 are set out in Table I.

EXAMPLES 16–20 and Control 3

These examples and control were undertaken in order to demonstrate the criticality of the component (c) in relation to amounts included in the desired compositions.

A variety of amounts of the silane expressed by the formula

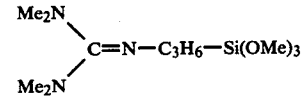

i.e., 0.005 part in Control 3, 0.05 part in Example 16, 0.2 part in Example 17, 0.5 part in Example 18, 1.0 part in Example 19 and 5.0 parts in Example 20, each were mixed with 100 parts of a dimethylpolysiloxane terminated at both chain ends with hydroxy groups having a viscosity of 30,800 centistokes at 25° C., 15 parts of the same fumed silica filler as used in Examples 10–15, 6.0 parts of vinyltri(isopropenyloxy)silane and 1.0 part of 3-aminopropyltriethoxysilane, to obtain respective compositions.

The tack-free time of the composition obtained from Control 3 was 24 hours, that from Example 16 180 minutes, that from Example 17 30 minutes, that from Example 18 5 minutes, that from Example 19 3 minutes and that from Example 20 2 minutes. The test results for these compositions and the cured rubbery elastomers formed thereof are set out in Table I.

Table I

| Example | Adhesivity kg/cm² | Mechanical properties | | | | | | | |
|---|---|---|---|---|---|---|---|---|---|
| | | As just cured | | | After 5 days | | | | |
| | | | | | at 150° C. | | | at 200° C. | | |
| | | H | TS | E | H | TS | E | H | TS | E |
| 1 | 3.4 | 28 | 22 | 410 | 29 | 23 | 400 | 32 | 20 | 390 |
| 2 | >7.6 | 30 | 23 | 380 | 32 | 25 | 390 | 36 | 29 | 360 |
| 3 | >12.3 | 32 | 28 | 320 | 38 | 25 | 290 | 42 | 21 | 260 |
| 4 | >10.6 | 26 | 21 | 530 | 28 | 22 | 510 | 31 | 19 | 450 |
| 5 | >8.6 | 35 | 16 | 400 | 41 | 18 | 290 | — | — | — |
| 6 | >9.4 | 32 | 20 | 340 | 35 | 21 | 310 | — | — | — |
| 7 | >9.1 | 31 | 19 | 390 | — | — | — | 35* | 16* | 310* |
| 8 | >7.4 | 23 | 15 | 580 | — | — | — | — | — | — |
| 9 | >13.5 | 30 | 26 | 410 | — | — | — | — | — | — |
| 11 | >8.4 | 30 | 24 | 510 | — | — | — | — | — | — |
| 12 | >11.2 | 32 | 25 | 460 | — | — | — | — | — | — |
| 13 | >10.9 | 33 | 26 | 440 | — | — | — | — | — | — |
| 14 | >10.4 | 35 | 24 | 410 | — | — | — | — | — | — |
| 15 | >8.2 | 43 | 18 | 340 | — | — | — | — | — | — |
| 16 | >8.6 | 22 | 20 | 450 | — | — | — | — | — | — |
| 17 | >10.8 | 30 | 23 | 490 | — | — | — | — | — | — |
| 18 | >12.1 | 31 | 25 | 520 | — | — | — | — | — | — |
| 19 | >10.6 | 33 | 24 | 500 | — | — | — | — | — | — |
| 20 | >9.4 | 28 | 20 | 460 | — | — | — | — | — | — |
| Control 1 | — | 36 | 14 | 280 | — | — | — | 82* | 20* | 25* |
| 3 | 5.0 | 18 | 15 | 440 | — | — | — | — | — | — |

Notes:
(1)In Adhesivity, rupture occurred in the body of the cured rubber per se and no ultimate adhesive strength could be determined in all examples but Example 1.
(2)H is hardness, TS tensile strength in kg/cm², and E ultimate elongation in %.
(3)*After 3 days at 250° C.

What is claimed is:

1. An organosilane or an organopolysiloxane having in a molecule at least one monovalent group represented by the general formula

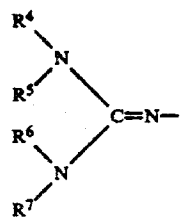 (I)

wherein $R^4$, $R^5$, $R^6$ and $R^7$ are each a hydrogen atom or a monovalent hydrocarbon group and the group represented by formula (I) is bonded to the silicon atom by a divalent group.

2. The organosilane of claim 1 having the formula

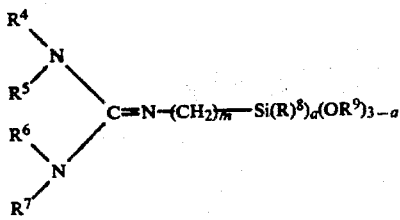

wherein
m is a positive integer of 1, 3, or 4,
a is 0, 1 or 2,
$R^4$, $R^5$, $R^6$ and $R^7$ are each the same as defined in claim 9,
$R^8$ is a monovalent hydrocarbon group having 1 to 6 carbon atoms, and
$R^9$ is an alkyl group having 1 to 4 carbon atoms, and a partial hydrolysis-condensation product thereof.

3. The organosilane of claim 2 wherein $R^4$, $R^5$, $R^6$, $R^7$, $R^8$, and $R^9$ each represents a methyl group, M is 3, and a is 0, 1 or 2

4. The organosilane of claim 3 having the formula

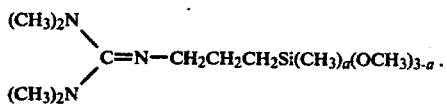

5. The organosilane of claim 1 selected from the group consisting of

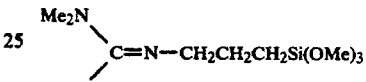

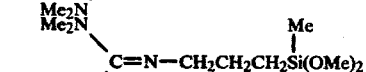

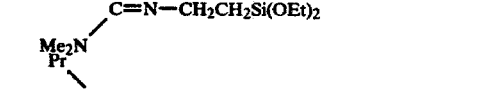

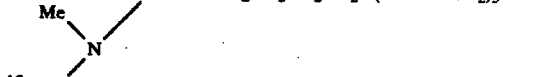

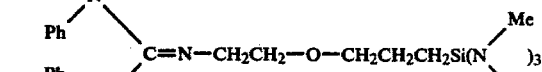

wherein Me is methyl, Et is ethyl, and Ph is phenyl.